United States Patent [19]

Van Iten et al.

[11] Patent Number: 5,188,625
[45] Date of Patent: Feb. 23, 1993

[54] SANITARY NAPKIN HAVING A COVER FORMED FROM A NONWOVEN WEB

[75] Inventors: Thomas P. Van Iten, Neenah; Howard A. Whitehead, Appleton; Julie A. Schindel, Oshkosh, all of Wis.

[73] Assignee: Kimberly-Clark Corporation, Neenah, Wis.

[21] Appl. No.: 569,317

[22] Filed: Aug. 17, 1990

Related U.S. Application Data

[63] Continuation-in-part of Ser. No. 61,844, Jun. 11, 1987, which is a continuation of Ser. No. 774,252, Sep. 9, 1985, abandoned.

[51] Int. Cl.$^5$ .............................................. A61F 13/15
[52] U.S. Cl. ................................. 604/383; 604/385.1
[58] Field of Search ............................ 604/383, 385.1

[56] References Cited

U.S. PATENT DOCUMENTS

| | | | |
|---|---|---|---|
| 2,115,122 | 4/1938 | Prudden | 99/77.1 |
| 2,332,848 | 10/1943 | Grabec | 154/2 |
| 2,748,863 | 6/1956 | Benton | 164/99 |
| 3,097,124 | 7/1963 | Denenberg | 154/44 |
| 3,104,998 | 9/1963 | Gelpke | 161/109 |
| 3,137,893 | 6/1964 | Gelpke | 18/4 |
| 3,161,554 | 12/1964 | Blackford | 156/242 |
| 3,227,854 | 1/1966 | Ramsey et al. | 219/244 |
| 3,344,789 | 10/1967 | Arnold et al. | 128/287 |
| 3,403,681 | 10/1968 | Hoey et al. | 128/290 |
| 3,542,634 | 11/1970 | Such et al. | 161/88 |
| 3,675,654 | 7/1972 | Baker et al. | 128/287 |
| 3,843,478 | 10/1974 | Zuscik | 161/164 |
| 3,929,135 | 12/1975 | Thompson | 128/287 |
| 3,939,836 | 2/1976 | Tunc | 604/370 |
| 3,949,127 | 4/1976 | Ostermeier et al. | 428/137 |
| 3,965,906 | 6/1976 | Karami | 128/287 |
| 3,967,623 | 7/1976 | Butterworth et al. | 128/287 |
| 4,079,739 | 3/1978 | Whitehead | 128/290 R |
| 4,100,324 | 7/1978 | Anderson et al. | 428/288 |
| 4,128,679 | 12/1978 | Pohland | 428/131 |
| 4,135,021 | 1/1979 | Patchell et al. | 428/134 |
| 4,151,240 | 4/1979 | Lucas et al. | 264/504 |
| 4,184,498 | 1/1980 | Franco | 128/290 R |
| 4,192,311 | 3/1980 | Felfoldi | 128/287 |
| 4,219,376 | 8/1980 | Roman | 156/209 |
| 4,248,822 | 2/1981 | Schmidt | 264/154 |
| 4,276,336 | 6/1981 | Sabee | 428/132 |
| 4,321,924 | 3/1982 | Ahr | 128/287 |
| 4,323,069 | 4/1982 | Ahr et al. | 128/287 |
| 4,324,246 | 4/1982 | Mullane et al. | 128/287 |
| 4,340,563 | 7/1982 | Appel et al. | 264/518 |
| 4,341,217 | 7/1982 | Ferguson et al. | 128/290 W |
| 4,342,314 | 8/1982 | Radel et al. | 128/287 |
| 4,397,644 | 8/1983 | Matthews et al. | |
| 4,469,734 | 9/1984 | Minto et al. | 428/134 |
| 4,634,440 | 1/1987 | Widlund et al. | 604/383 |
| 4,886,632 | 12/1989 | Van Iten et al. | 264/156 |

FOREIGN PATENT DOCUMENTS

| | | |
|---|---|---|
| 0164740 | 12/1985 | European Pat. Off. . |
| 0165807 | 12/1985 | European Pat. Off. . |
| 2204855 | 8/1973 | Fed. Rep. of Germany . |
| 1534042 | 6/1967 | France . |
| 1132120 | 10/1968 | United Kingdom . |
| 1229121 | 4/1971 | United Kingdom . |
| 1287063 | 8/1972 | United Kingdom . |
| 1296024 | 11/1972 | United Kingdom . |
| 1308677 | 2/1973 | United Kingdom . |
| 1393426 | 5/1975 | United Kingdom . |
| 1408009 | 10/1975 | United Kingdom . |
| 2103933A | 3/1983 | United Kingdom . |
| 2175026A | 11/1986 | United Kingdom . |

Primary Examiner—Randy C. Shay
Attorney, Agent, or Firm—Thomas J. Connelly

[57] ABSTRACT

A sanitary napkin is disclosed which has an absorbent and a fluid-permeable cover positioned over at least one surface of the absorbent. The cover is formed from a nonwoven web having a network of essentially unbroken thermoplastic fibers. The web has a plurality of apertures formed therethrough which are located in a predetermined area which represents less than about 80% of the surface area of the cover. Each of the apertures is surrounded by a consolidated ring formed of thermally set thermoplastic fibers which in turn is surrounded by a raised area which contacts the body of the user. The apertures formed in the web occupy about 20% to 55% of the predetermined area and permit body fluid to quickly pass through to the absorbent.

14 Claims, 8 Drawing Sheets

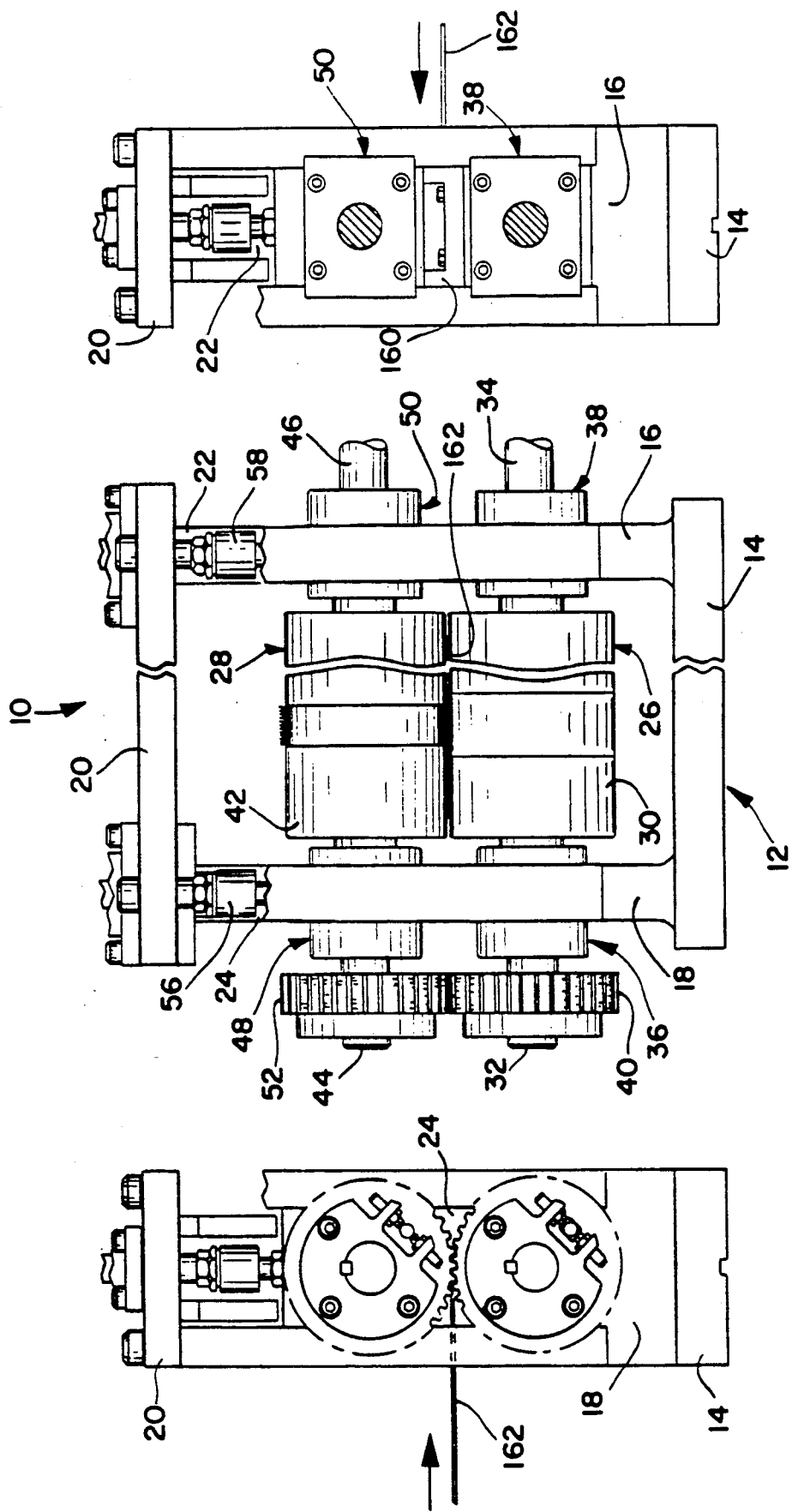

SANITARY NAPKIN HAVING A COVER FORMED FROM A NONWOVEN WEB

This application is a continuation-in-part of U.S. Ser. No. 07/061,844, filed Jun. 11, 1987 which in turn is a continuation of U.S. Ser. No. 06/774,252, filed Sep. 9, 1985 now abandoned.

FIELD OF THE INVENTION

This invention relates to a sanitary napkin having a cover made from a nonwoven web, and more particularly to a web having a predetermined area which is apertured so as to create openings which occupy about 20% to 55% of the predetermined area.

BACKGROUND OF THE INVENTION

Feminine pads, also referred to as sanitary napkins, such as those described in U.S. Pat. Nos. 4,397,644 and 4,079,739, are well known. Sanitary napkins of the prior art are normally of multilayered construction including: a fluid-absorbent core interposed within a fluid-impermeable baffle and a fluid-permeable cover. The cover being designed to transmit menstrual fluid or the like across its boundary to the absorbent core. As those skilled in the art will readily appreciate, the interrelationship of components is substantially more intricate; however, for purposes of basic understanding, the foregoing suffices. Within those very general parameters, one may also profitably compare the contoured sanitary napkin disclosed in U.S. Pat. No. 4,184,498.

Conventional sanitary napkins typically comprise an absorbing layer made of a hydrophilic absorbent material such as absorbent paper, absorbent cotton, pulverized pulp or the like, so that when having absorbed therein a large quantity of body fluid, the napkin becomes sticky on its surface. In addition, when the absorbing layer is subjected to pressure, the body fluid once absorbed therein is likely to ooze or flow out in a reverse direction toward the body of the wearer and can cause a sticky surface. Thus, the uppermost layer of the sanitary napkin becomes very uncomfortable to use and unsanitary. This problem is particularly apparent when body fluid is discharged in large quantities within a relatively short period of time in the initial stage of menstruation. Sometimes the absorbing layer is unable to fully absorb the discharge thereby permitting the body fluid to remain on the surface of the absorbing layer and allowing sideways leakage when the layer is subjected to varying body pressures.

Even at times of light flow, however, body fluids do not necessarily readily pass through the fluid-permeable cover into the fluid-absorbent core of the sanitary napkin. It has been recognized that menses is a complex fluid with uterine blood being only one component of its composition. Menses also contains cellular debris and a mucus-like fraction. The composition of menses has a significant effect on the transport of fluid from the cover into the absorbent matrix of a sanitary napkin, especially for certain women who consistently have high viscosity menses and comparatively low flow volumes. High viscosity menses tends to stay on the upper surface of the cover of the sanitary napkin.

The cover, or top layer of a sanitary napkin, is an important structural component respecting overall product efficacy, both objectively and subjectively from the user's point of view. A number of dichotomies become apparent when describing the ideal or preferred top layer of sanitary napkins. For consumer acceptance, a cloth-like texture and feel are preferred. In addition, the top layer should appear clean, dry and stain-free even during use. Thus, the cover layer should remain aesthetically pleasing even during use. Nonwoven webs which most economically and effectively achieve the objective of an acceptable cloth-like texture are, however, generally undesirable when evaluated on their ability to remain clean, dry and stain-free during use. With nonwoven webs, menses tends to get hung up or remain on the top layer while never reaching the lower absorbent layer since the fibers often act to block the path to the absorbent layer. Thus, the sanitary napkin becomes uncomfortable, wet, sticky and generally non-aesthetical.

SUMMARY OF THE INVENTION

Briefly, this invention relates to a sanitary napkin which has an absorbent and a fluid-permeable cover positioned over at least one surface of the absorbent. The cover is formed from a nonwoven web having a network of essentially unbroken thermoplastic fibers. The web has a plurality of apertures formed therethrough which are located in a predetermined area which represents less than about 80% of the total surface area of the cover. Each of the apertures is surrounded by a consolidated ring formed of thermally set thermoplastic fibers which in turn is surrounded by a raised area which contacts the body of the user. The apertures formed in the web occupy about 20% to 55% of the predetermined area and permit body fluid to quickly pass through to the absorbent.

The general object of this invention is to provide a sanitary napkin having a cover formed from a nonwoven web. A more specific object of this invention is to provide a sanitary napkin with a cover formed from a nonwoven web containing a predetermined area which is apertured.

Another object of this invention is to provide a sanitary napkin having a cover made from a nonwoven web wherein a predetermined area of the web is apertured and the apertures occupy about 20% to 55% of the predetermined area.

Still, another object of this invention is to provide a sanitary napkin having a cover which is formed from a nonwoven web which contains at least two layers.

Still further, an object of this invention is to provide a sanitary napkin with an improved cover.

Other objects and advantages of the present invention will become apparent to those skilled in the art in view of the following description and the accompanying drawings.

BRIEF DESCRIPTION OF THE DRAWINGS

FIG. 1 is a cross-sectional view through the length of the rotary perforating apparatus of the present invention.

FIG. 2 is a partial cross-sectional view through the drive side of the apparatus shown in FIG. 1.

FIG. 3 is a partial cross-sectional view through the operator side of the apparatus shown in FIG. 1.

DETAILED DESCRIPTION OF THE PREFERRED EMBODIMENTS

Figure 4:
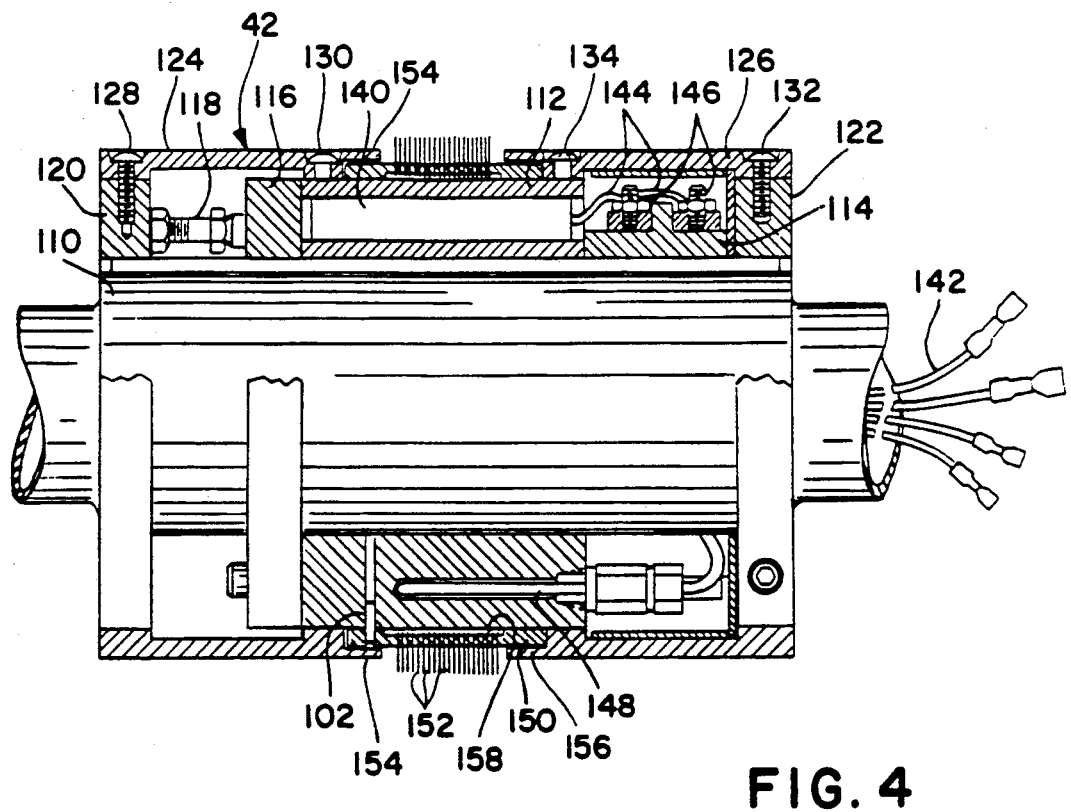
FIG. 4 is a cross-sectional view through the pin roll of the apparatus shown in FIG. 1.

Any type of nonwoven web comprising fusible polymeric fibers or filaments is useful in the practice of the present invention. For instance, a suitable nonwoven web cover material is a uniform spunbonded nonwoven web having one and one-half denier or larger fibers or filaments. Such a material is described in U.S. Pat. No. 4,340,563, to which reference is made for a fuller description of such material. This material is also referred to as linear drawn spunbond (LDS).

Alternatively, a bonded carded web is useful in the practice of the present invention. The bonded carded web is generally composed of 100% polypropylene, however, blends containing rayon, polyester and the like are equally suitable. Hollow fiber types may also be present in the bonded carded web. The bonded carded web is generally in the range of about 10 to about 50 grams per square meter (gsm) and is preferably within the range of about 18 to 24 gsm. The bonded carded web fibers range from about one and one-half to about three denier. The staple length is within the range of about 1.5 to 2 inches. Alternatively, the bonded carded web may be laminated to a film of ethyl methacrylate.

Another suitable nonwoven web is a "coform" material as described in U.S. Pat. No. 4,100,324. Coform is a blend of meltblown microfibers and an absorbent fiber such as pulp fluff. Representative meltblown fibers include polypropylene, polyethylene, polyethylene terephthalate, polyamide, acrylic and nylon fibers or blends. Alternatively, the coform may be laminated to a spunbonded nonwoven web.

A sanitary napkin cover, such as that described in U.S. Pat. No. 4,397,644, is also useful in the practice of the present invention. The material described therein is primarily a nonwoven thermoplastic web which is of sufficiently open structure to enhance the transfer of menses into an absorbent layer. Bonding is used to accomplish integration. This may be achieved by the application of heat, such as hot calendar embossing, or by ultrasonic means. Alternatively, the bonding may be accomplished by mechanical manipulation of the fibers without heat, as in needling. Ultrasonic bonding is particularly preferred. This nonwoven web is typically comprised of a polyester and polypropylene combination, typically 30% and 70% respectively. Alternatively, it may be comprised of 100% polypropylene. Hollow fiber types may also be present. This nonwoven web is a carded web which is generally in the range of about 30 to 150 gsm. Preferably, this nonwoven web ranges from about 40 to 120 gsm. This material ranges from about one and one-half to about eight denier and may be of high crimp nature thus giving it greater loft. Preferably, it is within the range of about 3 to 8 denier. The staple length is also within the range of about one and one-half to about three inches. This material may alternatively be laminated to spunbonded web.

In particular, suitable fusible fibers for this invention are; Vinyon, a vinyl chloride/vinyl acetate copolymer sold by Celanese Fiber Division and formerly by Avtex Fibers, Inc., of New York, N.Y.; Eastman 410 amorphous or crystalline polyester fibers sold by Eastman Chemical Products, Inc., a Subsidiary of Eastman Kodak Co., Kingsport, Tenn.; or Chisso ES a bicomponent polypropylene/ polyethylene fiber sold by Chisso Ltd., Osaka, Japan which, due to its differential melting point for each component of the fiber, could be used as the only thermoplastic fiber as well as in blends with other fibers.

A cylinder which would simply punch holes through and displace fiber is easily achieved. However, the nonwoven web material typically has a memory and thus a strong tendency to return to its original position and thereby close the hole which was just formed. It has been found that heating the tips of the pin to heat the nonwoven web during penetration acts to heat the fusible polymeric filaments near the area of the pin hole. The polymeric filaments are heated to a temperature just below the point of melting and cooled to room temperature after the pin is removed. This produced the consolidated area 168 seen in FIGS. 12 and 13. The consolidated rings 168 preferably have a diameter at least twice the diameter of the apertures formed in the web 162. The fusible thermoplastic fibers used in the nonwoven web are meltable and, if sufficient heat and pressure are applied to this nonwoven material, select areas will consolidate or tend to melt and lose the fibrous network characteristics of nonwoven materials. Under magnification of 20×, the material appears glassine, almost glass-like in appearance. The consolidated rings and apertures create a region which is more hydrophilic than the non-perforated surface of the web and therefore attracts fluid into these perforations. Of course, it is possible that some areas will actually melt and fuse during the course of the subject operation, but this is deemed to be less desirable in the practice of the present invention.

It is also relevant to note that it is not desirable to simply make a hole that removes or evaporates the material previously in the hole or aperture area and thus leaving a solid clean hole in the fabric. The goal of the present invention is to allow all of the material or nonwoven fabric to remain in the web because it is desirable to create some type of depth to the point of penetration. This depth or three dimensional profile is desirable since it allows a perception of thickness or texture to the nonwoven fabric.

Figure 12:
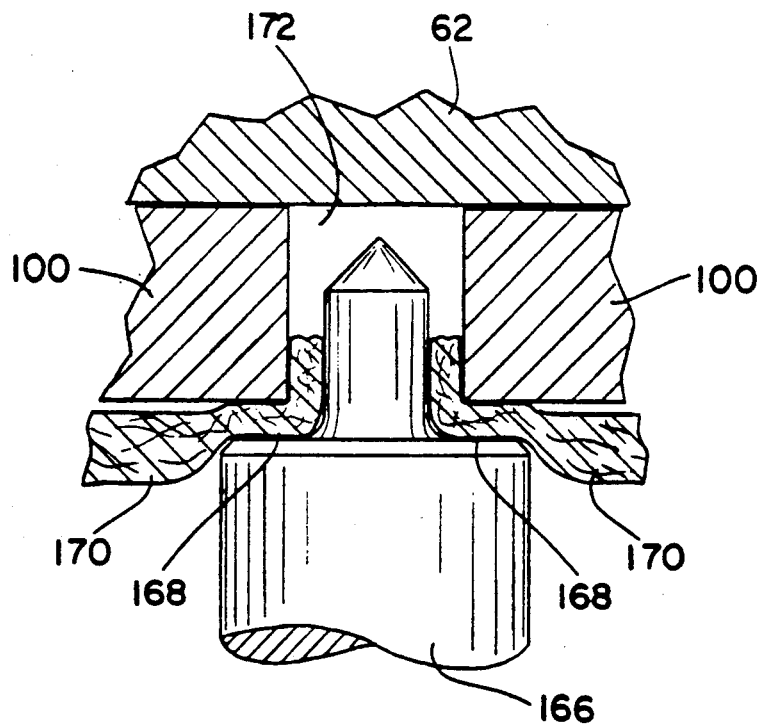
FIG. 12 is a cross-sectional view of a shouldered pin shown to be perforating an area of nonwoven web comprising thermoplastic fibers.
Figure 13:
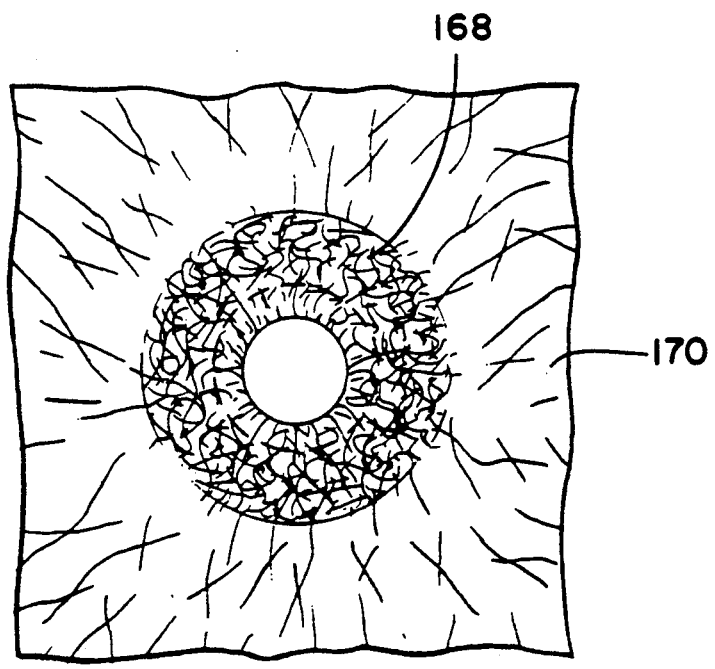
FIG. 13 is a view from the bottom of the nonwoven web of FIG. 12 after the pin has been removed.

Ideally, by making the apertures in the nonwoven web in the manner taught by the present invention, the raised ridges 170 are formed around the periphery of the dense consolidated portions 168, see FIGS. 12 and 13. The nonwoven material which has not become consolidated or densified is fluffier and thicker and therefore appears like a ridge or raised area 170 adjacent the consolidated ring 168. This ridged area 170 is ideally considerably less acceptable to fluid or menses since the menses can readily get hung up or stuck on the upper surface of the ridged portion 170 and be unable to enter the absorbent below. Generally, the heavier the fabric, the higher the ridge 170 will be. Since the consolidated rings 168 and apertures present a more hydrophilic area, the menses will be attracted to these areas and will readily pass through the apertures directly into the absorbent below.

Preferably, the heated pin makes a distinct, true hole through the nonwoven fabric. That is, no fibers remain in the hole itself. The hole should be free from any extraneous fibers or impurities. If a glob of fluid enters an aperture blocked by a few fibers, the glob of fluid could get hung up on the top of the nonwoven web and remain in that position blocking the entrance to the hole. This is obviously undesirable since it leaves an undesirable stain and wetness on the surface of the nonwoven cover.

The side walls of the apertures formed in the nonwoven web are aligned at an angle of approximately 90 degrees to the top horizontal plane of the web.

The apparatus of the present invention may be envisioned as any type of perforating device having a first member containing a series of pins and a second member containing a series of indentions or apertures for receiving entry of the pins. Preferably, the apparatus is a rotary perforating system with the capability of generating a combination of holes having a variety of shapes and in a wide range of patterns with a single pass of the nonwoven web through the system. The perforating system can be described as a system comprising two or more cylinders mounted in a configuration such that one or more cylinders are associated with the peripheral surface of a single apertured cylinder.

The apertured cylinder can be described as a hole roll which has been machined or engraved for finished female pattern design. The hole roll is heated internally and the surface is hardened to withstand embossing pressure.

A pin roll is also machined to a finished male pattern design for perforating the web. This matches the hole roll and is equipped with tools; for example, perforating pins, embossing pins or a combination of both. The pin roll is also heated internally.

Referring to FIGS. 1–3, a perforating apparatus 10 is shown having a frame 12 which includes a horizontal base 14, a pair of vertical side walls 16 and 18, and a top member 20 extending across the upper end of the side walls. The side walls 16 and 18 include vertical slots 22 and 24, respectively. Mounted within the slots are a pair of roll assemblies 26 and 28. The lower assembly 26 includes a hollow roll 30 and a pair of support shafts 32 and 34 extending coaxially from opposite ends of the lower roll 30. The shaft 32 is retained in a bearing mechanism 36 mounted in the slot 24 of the side wall 18. The shaft 32 projects completely through the slot 24 and is operably connected to a toothed gear 40. The other shaft 34 extends completely through the slot 22 and is retained in bearing housing 38. The shaft 34 is of a hollow construction for the purpose of receiving electrical conduits as will be hereinafter explained.

The upper roll assembly 28 includes a pin roll 42 and a pair of support shafts 44 and 46 extending longitudinally coaxially from opposite ends thereof. The shaft 44 is retained in a bearing mechanism 48 which is mounted in the slot 24, and the shaft 46 is retained in a bearing mechanism 50 which is mounted in the slot 22.

The shaft 44 projects completely through the slot 24 and is operably connected to a toothed gear 52 which engages the gear 40. There is a zero backlash arrangement. The shaft 44 may be driven by a power source (not shown) through a controllable speed device. The other shaft 46 extends completely through the slot 22 and is hollow in order to receive electrical conduits as will be hereinafter explained.

Referring to FIG. 3, a spacer 160 is shown which is used to adjust the clearance between the rolls 30 and 42. The spacer 160 determines the amount of penetration obtained by the pins into the hole roll 30.

Referring again to FIG. 1, the bearing mechanisms 48 and 50 are each vertically adjustable within the respective slots 24 and 22 by turnbuckle type connectors 56 and 58. The connectors 56 and 58 enable the upper or pin roll 42 to be raised or lowered relative to the hole roll 30 in order to change the vertical depth of the nip defined between the rolls 30 and 42, and also for maintenance and replacement of parts.

Figure 5:
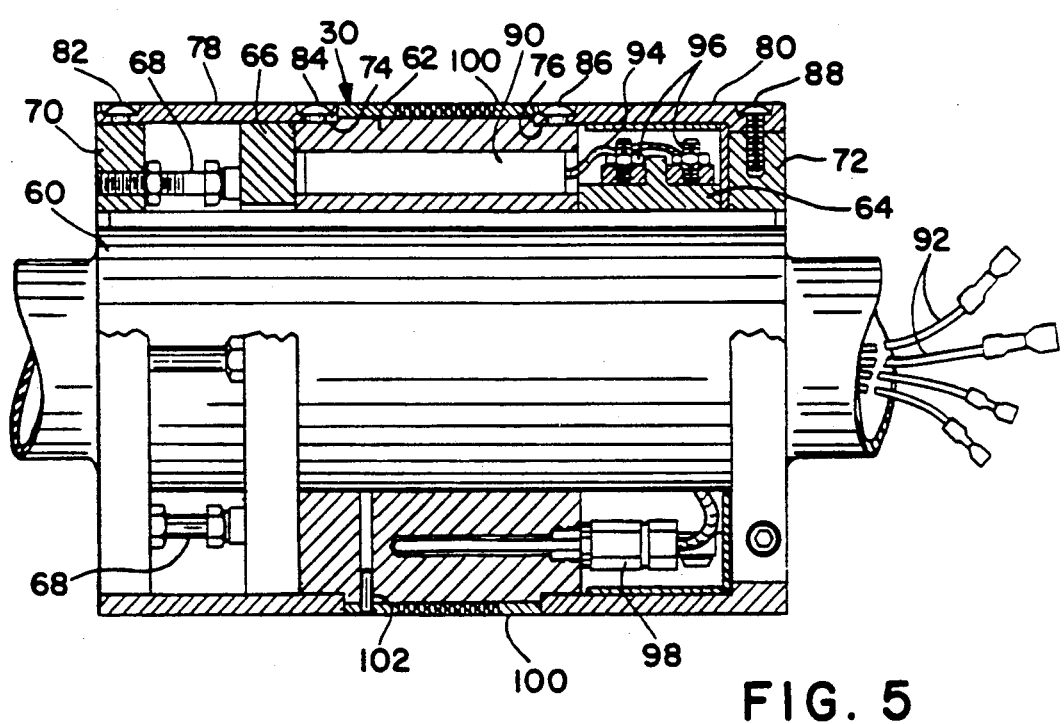
FIG. 5 is a cross-sectional view through the hole roll of the apparatus shown in FIG. 1.
Figure 6:
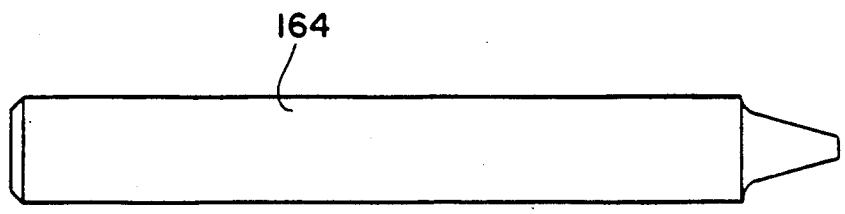
FIGS. 6 through 11 are views of various types of pins which are useful in the practice of the present invention.
Figure 7:
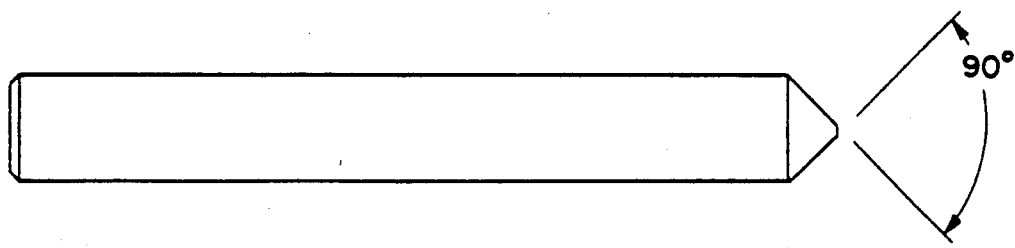
Figure 8:
Figure 9:
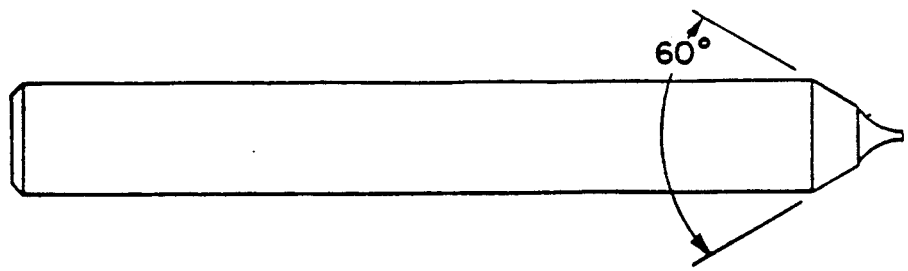
Figure 10:
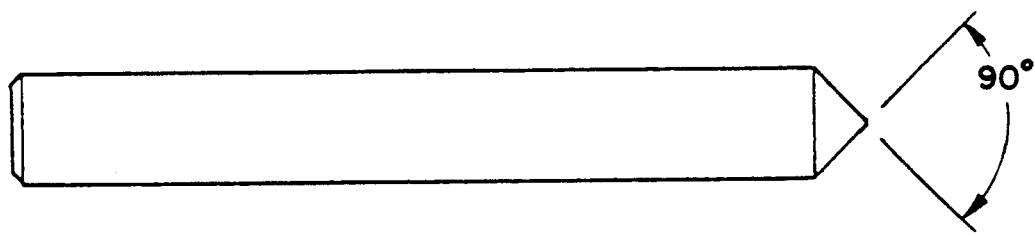

Referring to FIG. 5, the lower roll 30 contains an arbor 60 upon which a sleeve 62 is mounted by a keyway (not shown). The sleeve 62 is formed of a heat conducting material, typically brass, steel or aluminum. The preferred material is aluminum. The sleeve 62 is axially sandwiched between a terminal ring 64 and a retaining ring 66. The retaining ring 66 is pushed against the sleeve 62 by turnbuckle type connectors 68 which extend between the retaining ring 66 and an end ring 70. The end ring 70, in turn, is mounted on the arbor 60. The terminal ring 64 is positioned axially between the sleeve 62 and a second end ring 72 which is also mounted on the arbor 60.

The outer periphery of the sleeve 62 is stepped at its ends to define a pair of annular shoulders 74 and 76 which receive the inner ends of a pair of cover rings 78 and 80. A cover ring 78 engages the shoulder 74 and the outer peripheries of both the end ring 70 and the retaining ring 66. The cover ring 78 is suitably fastened to the end ring 70 and to the sleeve 62 by fasteners 82 and 84. A second cover ring 80 engages the shoulder 76 and the outer periphery of the end ring 72 and is suitably fastened thereto by fasteners 86 and 88.

The sleeve 62 contains a cartridge heater 90 which is electrically connected to an external power source (not shown) via electrical conduits 92 and 94 which are interconnected to terminals 96 carried by the terminal ring 64. The cartridge heater 90 provides heat to the sleeve 62. The sleeve 62 also carries a conventional temperature probe 98 for monitoring the temperature of the sleeve 62.

Mounted on the outside periphery of the sleeve 62 is a cylindrical strip 100. The strip 100 is formed of a heat conducting material such as brass, steel or aluminum. The preferred material is aluminum. The strip 100 is mounted on the sleeve 62 by a press fit, and a roll pin 102 is inserted through both the strip 100 and the sleeve 62 to prevent relative circumferential movement therebetween. Axial movement of the strip 100 is prevented by the cover sleeves 78 and 80 which bear against the axial ends of the strip 100. The strip 100 contains a series of tiny apertures or sockets 101 arranged in a pre-set pattern for reasons to be explained hereinafter. Preferably, each aperture 101 is round or circular in configuration and is sized to receive a corresponding pin 152 mounted on the upper roll 42.

Referring to FIG. 4, the upper roll 42 contains an arbor 110 upon which a sleeve 112 is mounted in the same manner as the sleeve 62 is mounted on the lower roll 30. The sleeve 112 is formed of a heat conducting material, such as brass, steel or aluminum, and is axially sandwiched between a terminal ring 114 and a retaining ring 116. The retaining ring 116 is pushed against the sleeve 112 by turnbuckle type connectors 118 which extend between the retaining ring 116 and an end ring 120 which is mounted on the arbor 110. The terminal ring 114 is positioned axially between the sleeve 112 and another end ring 122 mounted on the arbor 110.

Extending around opposite ends of the arbor 110 are a pair of cover sleeves 124 and 126. The cover sleeve 124 is secured to the outer peripheries of both the end ring 120 and the sleeve 112 by fasteners 128 and 130. The cover sleeve 126 is secured to the outer peripheries of both the end ring 122 and the sleeve 112 by fasteners 132 and 134.

The sleeve 112 contains a cartridge heater 140 which is electrically connected to an external power source (not shown) via electrical conduits 142 and 144. The conduits 142 and 144 are interconnected to terminals 146 carried by the terminal ring 114. The cartridge heater 140 provides heat to the sleeve 112. The sleeve 112 also caries a conventional temperature probe 148 for monitoring the temperature of the sleeve 112.

Mounted on the outside periphery of the sleeve 112 is a cylindrical strip 150 formed of a heat conducting material such as brass, steel or aluminum. The preferred material is aluminum. The strip 150 is mounted on the sleeve 112 by a press fit, and a roll pin 102 is inserted through both the strip 150 and the sleeve 112 to prevent relative circumferential movement therebetween. Lip portions 154 and 156 of the cover sleeves 124 and 126 overlie the edges of the strip 150 to aid in the retention thereof.

The strip 150 carries a plurality of needles or pins 152 which project outwardly beyond the outer peripheries of the cover sleeves 124 and 126 by a distance greater than the depth of the nip between the rolls 30 and 42 so that the ends of the pins 152 enter the apertures 101 formed in the lower roll 30. To that end, the apertures 101 are arranged in register with the pins 152 and have a wider diameter than the pins 152 to prevent the pins 152 from contacting the walls of the apertures 101. It will be appreciated from the foregoing that the upper roll 42 may be designated as a pin roll and the lower roll 30 as a hole roll. Preferably, the pins 152 are formed of a heat conductive material such as brass or steel. The pins 152 are mounted within the strip 150 by placement either from the inside of or from the outside of the cylinder. Placement of the pins 152 on the outside of the cylinder generally requires a space for setting of the pins 152 and the use of a type of compound that, upon filling the space, provides an element of permanence to the setting, thereby not allowing the pins 152 to be removed. The strip 150 includes a recess 158 facing the sleeve 112 to receive the inner ends of the pins 152. The pins 152 project in radial outward directions with respect to the axis of rotation of the pin roll 42. The apertures 101 formed in the strip 100 project in corresponding directions so as to be able to receive the ends of the pins 152.

It will be appreciated that the pins 152 are heated by conduction due to contact between the heated sleeve 112 and the strip 150 and between the strip 150 and the inner ends of the pins 152. The corresponding hole roll 30 is heated in a similar manner. In operation, the rolls 30 and 42 are synchronously rotated while a web 162 of fabric is fed through the nip defined by the rolls. As this occurs, the pins 152 contact and completely penetrate the fabric, separating the individual fibers to form a generally cylindrical hole through the fabric. Since the pins 156 are heated, the fibers which are displace by each heated pin will be consolidated, compressed or otherwise densified and set in that glassine-like configuration so that the hole cannot re-close. Thus, the fibrous web is autogenously bonded; that is, does not require the use of an adhesive to form structurally stable apertures. Some portion of the fibers being pushed will enter the associated opening in the hole roll 30, whereby dense consolidated rings 168 and annular ridge 170 will be formed around each of the holes. Such consolidated rings 168 and raised ridges 170 serve to add depth to the web and thereby improve the cloth-like texture and feel.

Since the pins 152 pass completely through the fabric and tend to thermally set any fibers with which they come into contact, it is assured that all of the holes will be unblocked. In other words, no fiber strands will remain which might extend across, and partially obstruct, the holes.

Nonwoven web fabric 162 may enter the apparatus 10 from either side of the two cylinders.

The foregoing describes a two cylinder configuration with a female patterned main cylinder and a male patterned worker cylinder. However, other embodiments are anticipated such as a three cylinder configuration where the three cylinders may or may not relate in a linear fashion. By using a multiple cylinder configuration a wider variety of patterns can be attained since different male or pin rolls 42 may be used. That is, the pin rolls 42 need not be of the same shape or diameter. This is best depicted in FIGS. 14, 14A, 14B and 14C wherein there are three different pin rolls 42.

At the outset, it is relevant to note that the temperature of the heated pin roll 42 may be higher than that of the hole roll 30 without departing from the spirit of the present invention. This is because approximately 10% of the heat from the pin roll 42 may be lost at the tips of the pins 152 but without a loss in overall operating or functional efficiency. Of course, the two rolls 30 and 42 may be maintained at about the same temperature. There is no easy means of actually heating the tips of the pins 152, thus, it is necessary to heat the pin roll 42 itself and via conduction drive heat to the pin head. The temperature of the pin roll 42 may generally be maintained in the range of about 110 degrees Fahrenheit to about 300 degrees Fahrenheit. The hole roll 30, on the other hand, may generally fall within the temperature range of about 90 degrees Fahrenheit to about 350 degrees Fahrenheit.

The speed of the rotary apparatus is generally within the range of about 12 feet to 220 feet per minute on nonwoven fiber. Since we are dealing with a rotary process, if parameters such as heat, angle of approach of the pin, and the like are controlled, speeds up to approximately 500 feet per minute could conceivably be achieved.

It may be considered suitable to thermally treat the nonwoven web 162 prior to processing. The web 162 may be pre-cooled or post-cooled, that is, cooled after undergoing the perforation operation.

Generally, if the speed of a nonwoven web 162 through the rotary apparatus is increased, the temperature must also be increased. These two parameters are directly related since the web 162 may actually burn if the temperature is too high and the pins 152 and the web 162 maintain contact for too long. Preferably, an electrical mechanism is used which is able to maintain both parameters of temperature and speed in the ideal or best relationship.

It is also particularly relevant to note that during the rotary operation, the pins 152 never touch the interior of the corresponding hole on the hole roll 30. The individual hole diameters in the hole roll 30 are preferably always approximately 0.010 inch larger than the diameter of the pin shaft. This is area 172 in FIG. 12. At a minimum, the hole diameter is selected to be non-binding respecting the size of the mating pin, typically at least 0.005 inch greater than the diameter of the pin shaft on the pin roll. This spacing is important in the practice of the present invention in order to achieve the proper depth of the entry of the pin through the nonwoven web fabric. Otherwise, if the pin head was too long, it might touch the sides of the hole.

FIGS. 6–11 depict pins of varying sizes and shapes. Each of these pins is suitable for forming the apertures in the nonwoven web 162. Each pin may be located on a flat plate type device placed on some type of rotary cylinder as was previously described. The hole in the hole roll 30 need not be of the same shape as the pin or pin head. As long as the proper relative dimensions are maintained to preclude binding or interference, the hole may be less defined or more rounded than the pin shape.

Figure 11:
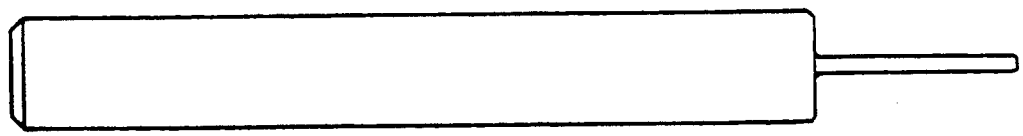
Figure 14:
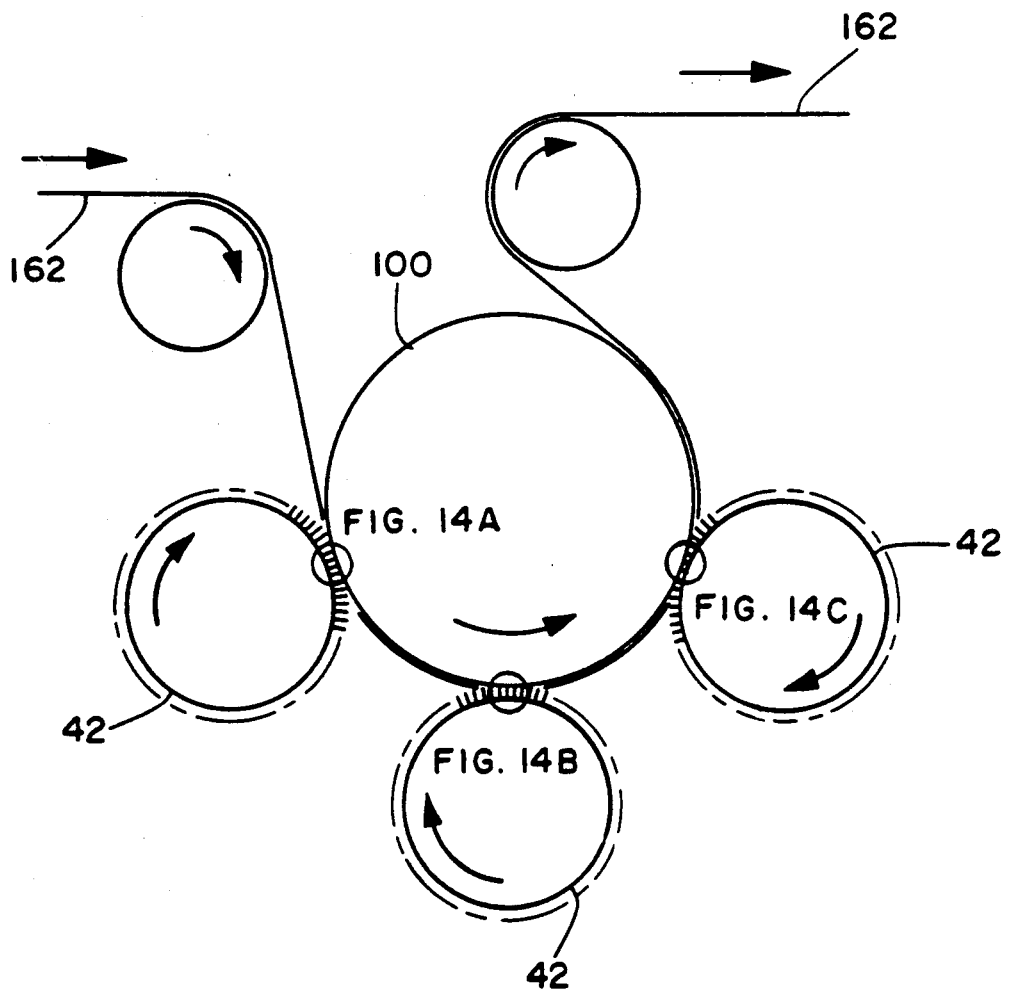
FIG. 14 is a cross-sectional view through the hole roll and each of the pin rolls is a multi-roll system showing the path of the nonwoven web.
Figure 14A:
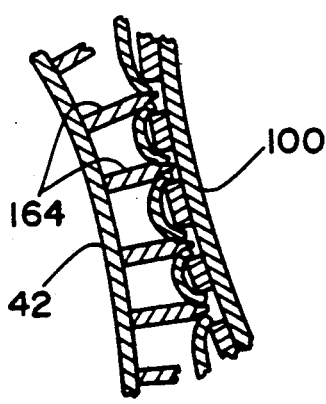
FIG. 14A is an enlarged view of a portion of FIG. 14 showing pins having a profile as depicted in FIG. 6 piercing the nonwoven web and entering into the apertures formed in the roll 100.
Figure 14B:
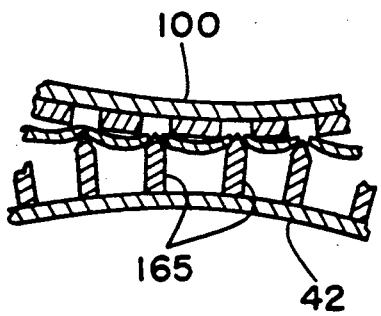
FIG. 14B is an enlarged view of a portion of FIG. 14 showing pins having a profile as depicted in FIG. 10 piercing the nonwoven web and entering into the apertures formed in the roll 100.
Figure 14C:
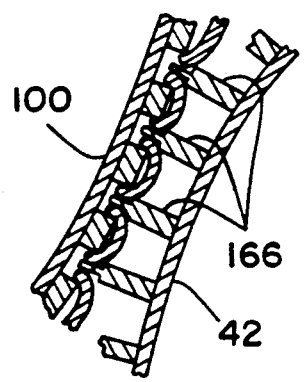
FIG. 14C is an enlarged view of a portion of FIG. 14 showing pins having a profile as depicted in FIG. 11 piercing the nonwoven web and entering into the apertures formed in the roll 100.

FIGS. 11, 12 and 14C depict a shouldered pin 166 which is a suitable pin in the practice of the present invention.

The exact shape and dimensions of the pin head are not critical for present purposes. However, the diameter of the shaft 164 of the pin is important. The shaft 164 of the pin is most relevant since it determines the diameter of the aperture which is formed. Generally, the diameter of the shaft of the pin ranges from about 0.015 to about 0.125 of an inch. Preferably, the pin shaft ranges from about 0.032 to about 0.097 of an inch. The pins essentially act to burst the nonwoven fabric while not actually damaging or breaking any of the fibers themselves.

The pin itself is comprised of a metal. Preferred metals include steel or brass, with steel being most preferred. Almost any type of steel can be used including hard or soft steel. Stainless steel is very suitable. The preferred metal is one which would allow the greatest heat transfer from the heated roll to the pin head.

A plastic pin or pin head may be desired in the practice of the present invention at the option of the designer. However, some plastics are generally not able to withstand the high operating temperatures as described herein and materials selection needs to be made accordingly.

Alternatively, the pin may comprise a metal core such as steel with a plastic surface. The plastic covering may be a coating or it may be a mechanically fit by pushing a covering onto the pin. The plastic coated metal pin concept is particularly advantageous since the plastic surface provides a smooth, slippery surface to the pin, thus allowing it to penetrate the nonwoven fabric more readily. A preferred coating material would be a fluoropolymer coating, in particular, polytetrafluoroethylene (Teflon ® by DuPont).

A metal pin may also be impregnated with plastic material. In this case, the metal surface must be porous enough to allow the actual impregnation of the plastic onto the metal. Suitable plastic materials for this impregnation include, but are not limited to, polypropylene, polyethylene and the like.

Every one of the pins must enter the matching hole on the hole roll 30 with perfect clearance. There is never any metal-to-metal, or in the case of plastic coated pins, plastic-to-plastic contact. The diameter of the shaft of the pin is generally in the range of 0.015 inch to about 0.125 inch. This is the true diameter of the tool, therefore, this value does not necessarily represent the diameter of the finished hole. The finished hole may be slightly oblong and slightly larger than the diameter of the pin shaft when completed. The exact diameter of the hole is dependent on a variety of factors that must be each independently determined.

In determining the number of apertures or holes per area on the nonwoven web 162, it is pertinent to discuss the percent of openness of a predetermined apertured area. This is a more meaningful value than the pin population per square inch since pin diameter varies so widely. The goal is to form a texture on the surface which has opening therein to allow fluid menses to penetrate more readily while at the same time minimizing a return of the fluid to the nonwoven cover. Maintaining a sanitary napkin which is aesthetically pleasing is thus a key to the present invention.

The cover is formed from a nonwoven web having a network of essentially unbroken thermoplastic fibers. The web has a plurality of apertures formed therethrough which are located in a predetermined area. The predetermined area represents less than about 80%, and preferably less than about 60%, of the surface area of the cover. The surface area of the cover can be defined as the available area of the cover which is designed to face the body of the wearer. Each of the apertures is surrounded by a consolidated ring formed of thermally set thermoplastic fibers. Each consolidated ring in turn is surrounded by raised areas which can contact the body of the wearer. The apertures occupy about 20% to 55% of the available surface area within the predetermined area. Preferably, the apertures occupy about 30% to 50%, more preferably about 40% to 50% of the surface area within the predetermined area. The upper practical limit seems to be approximately 55% due to mechanical and/or physical limitations of the system.

The pattern of the pins themselves may vary considerably. If a smaller shaft size is selected, a greater number of holes are necessary to achieve the same degree of openness.

It may also be advantageous to add a binder to the intact area of the nonwoven web. The intact area is that area between the apertures which has been referred as the raised or ridge area. The addition of a binder is beneficial in that the binder will not destroy the cloth-like texture and appearance of the nonwoven web but will fill the tiny voids within the ridges. This will prevent fluid from getting hung up and will provide a cleaner appearing cover. The binder may be applied at any stage of the process including during the formation of the nonwoven web, after the web is formed or during the time of forming apertures or consolidated rings. The binder must be able to withstand body temperature heat without melting or rubbing off. Suitable binders include polyethylene glycol and the like.

Another feature of this invention involves adding a color toner or pigment either to the predetermined apertured area or to the entire top surface of the sanitary napkin. The addition of a color toner or pigment has several advantages. Most significantly, it tends to affect perceptual or visual masking of fluid during use of the sanitary napkin. The coloring may thus attenuate the typical red menstrual stain observable during use. It also improves visual perception by emphasizing, in the case of a perforated nonwoven cover material, that the product is effective in achieving a degree of physical separation between the body of the wearer and the absorbent which contains the menstrual fluid. The coloring also makes the perforations more distinct and noticeable. The coloring or pigment is selective and may involve all or a portion of the nonwoven cover material. The preferred colors include those in the blue, blue-green, and green areas of the visual light spectrum. Alternatively, the toning or coloring agent may be already present in the binder. In addition, instead of adding the toner or pigment to the cover layer itself, a similar effect could be achieved by adding the toner or pigment to the absorbent material directly under the cover layer. If a more conventional white coloration is desired, a whitening or opacifying agent may be used such as titanium dioxide ($TiO_2$) up to a level of approximately 8% of the total weight of the cover material.

As previously indicated, the apertured nonwoven web 162 is suitable as the uppermost layer or cover of a sanitary napkin. The raised ridges 170, as shown in FIG. 12, face the peripheral area of the wearer when the nonwoven web is used as the cover material. Any sanitary napkin bearing a fibrous cover and currently known in the art may contain the apertured nonwoven web cover material of the present invention. In the simplest terms, a sanitary napkin contains an absorbent constructed of fibrous material or the like, a fluid-permeable cover and a fluid-impermeable baffle. A pressure sensitive attachment means is usually attached to the exterior surface of the baffle and serves to hold the sanitary napkin stationary to the crotch portion of an undergarment. The absorbent may include nay of the well-known materials currently known in the art, including wood pulp fluff, multiple layers of cellulose wadding, cotton or rayon fibers, cellulose sponge, hydrophilic synthetic sponge, and the like. A superabsorbent can also be added to the absorbent to increase its capacity to hold body fluid.

The fluid-impervious baffle is preferably a thin plastic film such as polyethylene or polypropylene of about one-half to three mils (i.e., thousandth of an inch) in thickness. Other thin flexible films such as polyvinylchloride, polyvinylidene chloride, natural rubber, etc., may be employed. Another useful material is a thin polyurethane film which may be of an open or close-cell construction on the interior. The film can be absorbent or nonabsorbent but should have a closed fluid-impervious skin on at least the bottom surface.

Exemplary of such a baffle is a conventional 0.4 oz. per square yard spunbonded web with a 0.75 mil (0.00075 inch) film of an ethylene methyl acrylate (EMA)k, preferably with the EMA side toward the body of the absorbent material.

According to this invention, the sanitary napkin is provided with improved comfort and the ability to relatively rapidly transfer viscous menses from the apertured nonwoven web cover into the absorbent below. The absorbent matrix described in U.S. Pat. No. 4,397,644 contains a principal absorbent component characterized by relatively high fluid retention and a second component including comfort enhancement capabilities positioned at least in part between the principal absorbent and the fluid-permeable cover or wrap. The second component, that is the cofort enhancing component, may be integrated with the apertured nonwoven web to provide intimate contact and densified regions. As a consequence, fluid transfer routes are established and fluid is conveyed to the principal absorbent component. This fluid transfer system may be used in association with the nonwoven web cover of the present invention.

Figure 15:
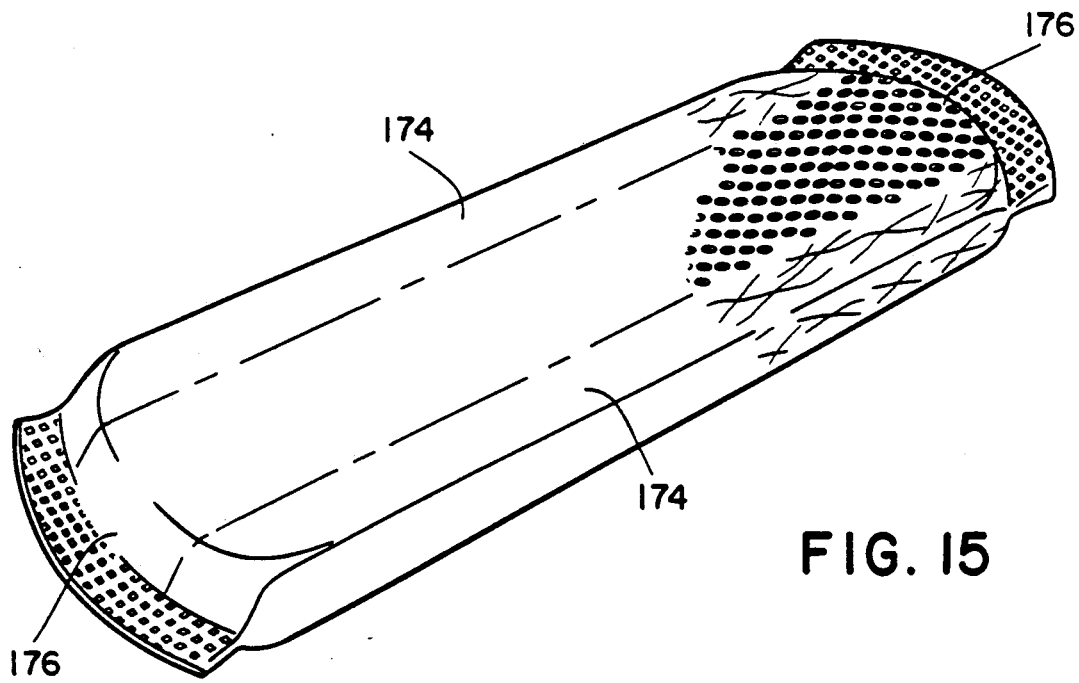
FIG. 15 is a plan view of the top or cover layer of a feminine sanitary napkin depicting the pattern of the perforations.

FIG. 15 shows a possible design or pattern for the apertures formed on a predetermined area of the cover. The predetermined apertured area 176 extends approximately the entire length of the sanitary napkin and has a width less than the overall width of the napkin. The predetermined apertured area 176 has a width of between about 1 to 2 inches and is flanked by a pair of non-apertured areas 174. The predetermined apertured area 176 should preferably have a length which is greater than about 60% of the length of the sanitary napkin so as to cover the perineum region of the wearer. For example, it is possible to construct a sanitary napkin about 6 to 12 inches long which has a predetermined apertured area with a length which terminates about ¾ of an inch from each end of the napkin.

Figure 16:
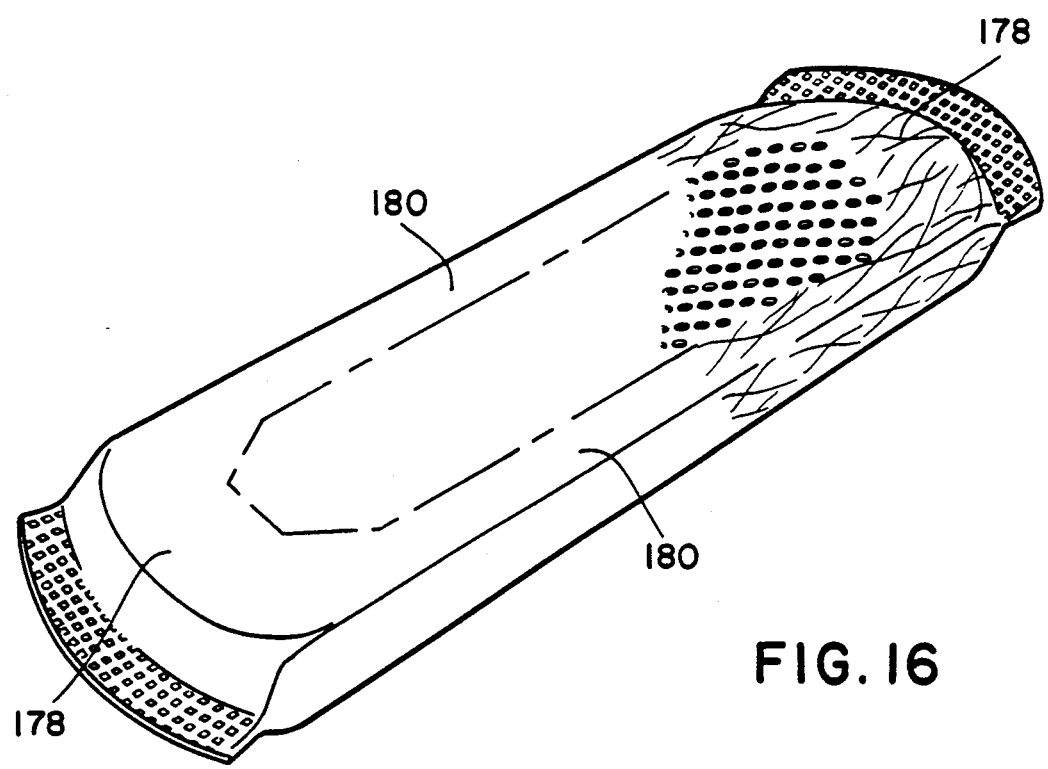
FIG. 16 is a plan view of the top or cover layer of another feminine sanitary napkin depicting the pattern of the perforations.

In FIG. 16, an alterative design is shown wherein the predetermined apertured area is surrounded by a non-apertured area 180 which extends about its periphery. The non-perforated area can vary in size but preferably is about ¾ to 2.0 inches wide. In FIG. 16, the predetermined apertured area has a length which is less than the entire length of the sanitary napkin.

Alternatively, a distinct registered pattern may be obtained on the cover of the sanitary napkin. An apertured pattern of approximately 1 to 2 inches wide need not extend the full length of the napkin, as shown in FIG. 15. Typically, the predetermined apertured area may terminate about ¾ to 2 inches from either of the longitudinally extending sides of the napkin or from the opposite ends of the napkin. In the case of a registered pattern, the predetermined apertured area is preferably located in and near the center of the napkin so as to be aligned with the perineum of the wearer.

Figure 17:
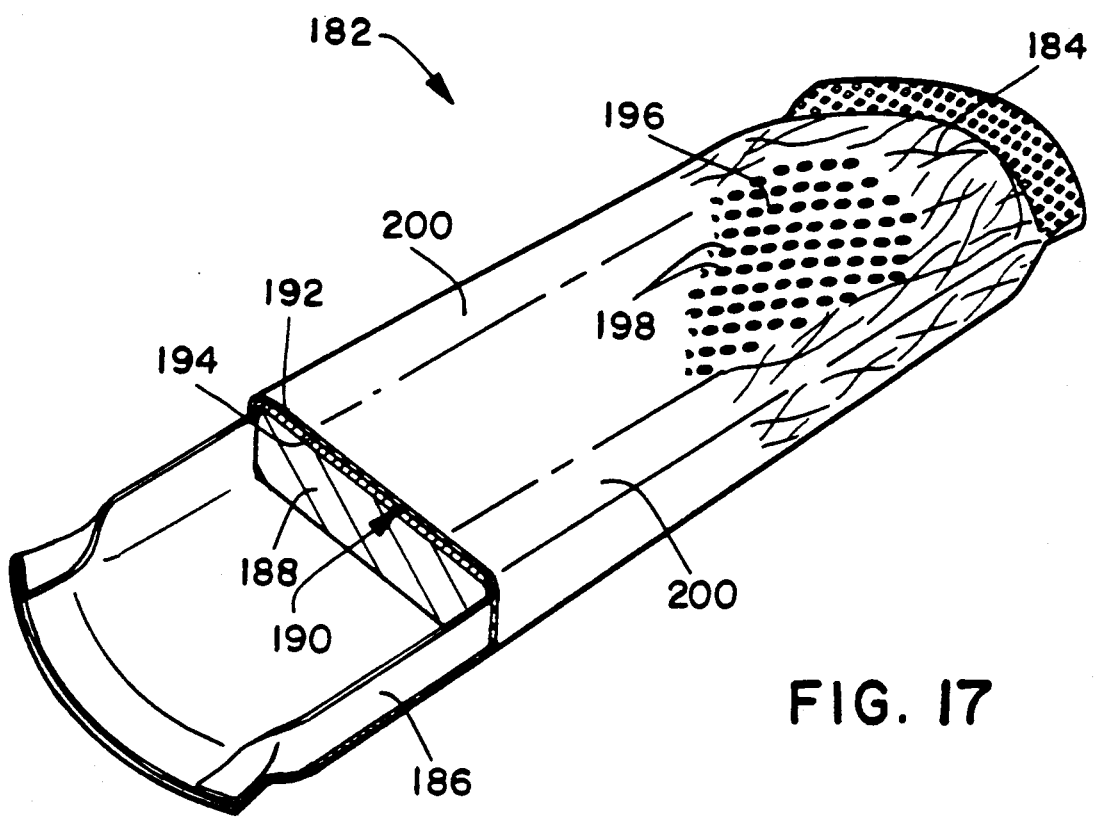
FIG. 17 is a partial cross-sectional view of a sanitary napkin showing an absorbent enclosed by a fluid-permeable cover and a fluid-impermeable baffle.

Referring to FIG. 17, a sanitary napkin 182 is shown constructed of a fluid-permeable cover 184, a fluid-impermeable baffle 186 and an absorbent 188 enclosed therebetween. The cover 184 is formed from a nonwoven web 190 which has two layers 192 and 194. The first layer 192 is composed of polypropylene spunbonded fibers and the second layer is a combination of pulp and polyethylene. Preferably, the spunbonded layer 192 forms the top layer which comes in contact with the body of the wearer. The two layers 192 and 194 can be laminated together. The web 190 has a predetermined apertured area 196 containing a plurality of apertures or holes 198. The apertures 198 extend completely through both layers 192 and 194 of the web 190. The predetermined apertured area 196 is surrounded by a non-apertured area 200 which makes up the remaining surface area of the cover 184.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. A sanitary napkin comprising:
   a) an absorbent; and
   b) a fluid-permeable cover positioned over at least one surface of said absorbent, said cover formed from a nonwoven web having a network of essentially unbroken thermoplastic fibers, said web having a plurality of apertures formed therethrough which extend completely through said cover and expose said absorbent, said apertures being located in a predetermined area representing less than about 80% of the surface area of said cover, and each of said apertures being surrounded by a consolidated ring formed of thermally set thermoplastic fibers, which in turn is surrounded by a raised area, wherein said apertures occupy about 30% to 55% of said predetermined area.

2. The sanitary napkin of claim 1 wherein said apertures occupy about 40% to 50% of said predetermined area.

3. The sanitary napkin of claim 1 wherein said web includes at least two layers, one of which is formed from spunbonded fibers and the other is a combination of pulp and polypropylene, and said plurality of apertures extend completely through both of said layers.

4. The sanitary napkin of claim 3 wherein said layers are laminated together.

5. The sanitary napkin of claim 1 wherein said predetermined area has a width of between about 1 to 2 inches.

6. The sanitary napkin of claim 1 wherein said predetermined area has a length approximately equal to the length of said sanitary napkin.

7. The sanitary napkin of claim 1 wherein said predetermined area has a length which is greater than about 60% of the length of said sanitary napkin.

8. The sanitary napkin of claim 1 wherein said predetermined area has a length which terminates about ¾ of an inch from the ends of said sanitary napkin.

9. A sanitary napkin comprising:
   a) a fluid-impermeable baffle;
   b) an absorbent positioned on said baffle; and
   c) a fluid-permeable cover cooperating with said baffle to enclose said absorbent, said cover positioned over at least one surface of said absorbent, said cover formed from a nonwoven web having a network of essentially unbroken thermoplastic fibers, said web having a plurality of apertures formed therethrough which extend completely through said cover and expose said absorbent, said apertures being located in a predetermined area which are void of any extraneous fibers, said predetermined area representing less than about 60% of the surface area of said cover, and each of said apertures being surrounded by a consolidated ring formed of thermally set thermoplastic fibers, which in turn is surrounded by a raised area, wherein said apertures occupy about 30% to 55% of said predetermined area.

10. The sanitary napkin of claim 9 wherein said apertures occupy about 40% to 50% of said predetermined area.

11. The sanitary napkin of claim 9 wherein said web includes at least two layers, one of which is formed from spunbonded fibers and the other is a combination of pulp and polypropylene, and said plurality of apertures extend completely through both of said layers.

12. The sanitary napkin of claim 9 wherein said raised areas surrounding said consolidated rings are designed to contact the body of the wearer.

13. A sanitary napkin comprising:
   a) an absorbent; and
   b) a fluid-permeable cover positioned over at least one surface of said absorbent, said cover formed from a nonwoven web having a network of essentially unbroken thermoplastic fibers, said web having a plurality of apertures formed therethrough which extend completely through said cover and expose said absorbent, said apertures being located in a predetermined area representing less than about 80% of the surface area of said cover, said apertures having side walls which are aligned approximately 90 degrees to an upper plane of said sanitary napkin and each of said apertures being surrounded by a consolidated ring formed of thermally set thermoplastic fibers, which in turn is surrounded by a raised area, wherein said apertures occupy about 30% to 55% of said predetermined area.

14. A sanitary napkin comprising:
   a) a fluid-impermeable baffle;
   b) an absorbent positioned on said baffle; and
   c) a fluid-permeable cover cooperating with said baffle to enclose said absorbent, said cover positioned over at least one surface of said absorbent, said cover formed from a nonwoven web having a network of essentially unbroken thermoplastic fibers, said web having a plurality of apertures formed therethrough which extend completely through said cover and expose said absorbent, said apertures being located in a predetermined area and which are void of any extraneous fibers, said predetermined area representing less than about 60% of the surface area of said cover, said apertures having side walls which are aligned approximately 90 degrees to an upper plane of said sanitary napkin, and each of said apertures being surrounded by a consolidated ring formed of thermally set thermoplastic fibers, which in turn is surrounded by a raised area, wherein said apertures occupy about 30% to 55% of said predetermined area, and
   d) a binder added to said fluid-permeable cover.

* * * * *

UNITED STATES PATENT AND TRADEMARK OFFICE
CERTIFICATE OF CORRECTION

PATENT NO. : 5,188,625

DATED : February 23, 1993

INVENTOR(S) : Thomas P. Van Iten, Howard A. Whitehead and Julie A. Schindel

It is certified that error appears in the above-identified patent and that said Letters Patent is hereby corrected as shown below:

Column 11, line 36, after the word the delete the word "peripheral" and insert --perineal-- therefore.

Signed and Sealed this

Thirteenth Day of September, 1994

Attest:

BRUCE LEHMAN

Attesting Officer

Commissioner of Patents and Trademarks